United States Patent
Peyman (10) Patent No.: US 8,903,468 B2
(45) Date of Patent: *Dec. 2, 2014

(54) LASER COAGULATION OF AN EYE STRUCTURE FROM A REMOTE LOCATION

(76) Inventor: Gholam Peyman, Sun City, AZ (US)

( * ) Notice: Subject to any disclaimer, the term of this patent is extended or adjusted under 35 U.S.C. 154(b) by 155 days.

This patent is subject to a terminal disclaimer.

(21) Appl. No.: 13/573,100

(22) Filed: Aug. 20, 2012

(65) Prior Publication Data

US 2012/0323228 A1     Dec. 20, 2012

Related U.S. Application Data

(63) Continuation-in-part of application No. 12/925,518, filed on Oct. 22, 2010, now Pat. No. 8,452,372.

(60) Provisional application No. 61/455,111, filed on Oct. 13, 2010.

(51) Int. Cl.
*A61B 5/05* (2006.01)
*A61F 9/008* (2006.01)

(52) U.S. Cl.
CPC ......... *A61F 9/00821* (2013.01); *A61F 9/00804* (2013.01); *A61F 9/00825* (2013.01); *A61F 2009/00846* (2013.01); *A61F 2009/00863* (2013.01)
USPC ........... 600/407; 600/425; 600/427; 600/476; 606/2; 606/4; 606/10; 606/11; 606/13; 700/2; 700/3; 700/28; 700/32; 700/33; 700/65

(58) Field of Classification Search
USPC ............ 600/407, 425, 427, 476; 606/2, 4, 10, 606/11, 13; 700/2, 3, 28, 32, 33, 65
See application file for complete search history.

(56) References Cited

U.S. PATENT DOCUMENTS

| | | |
|---|---|---|
| 4,213,678 A | 7/1980 | Pomerantzeff et al. |
| 4,247,176 A | 1/1981 | Ito |
| 4,736,744 A | 4/1988 | Koike et al. |
| 4,759,360 A | 7/1988 | Nakanishi et al. |
| 4,838,680 A | 6/1989 | Nunokawa |
| 5,049,147 A | 9/1991 | Danon |
| 5,572,266 A | 11/1996 | Ohtsuka |
| 5,713,047 A | 1/1998 | Kohayakawa |
| 5,742,374 A | 4/1998 | Nanjo et al. |
| 5,815,242 A | 9/1998 | Anderson et al. |
| 5,855,553 A * | 1/1999 | Tajima et al. .................. 600/407 |
| 5,923,399 A * | 7/1999 | Van de Velde ................ 351/221 |

(Continued)

OTHER PUBLICATIONS

Ertel et al., "Retinal Evaluation Efficacy of a Scanning Laser Ophthalmoscope (Optos P200): Compared to a Digital Retinal Camera," White Rock Optometry Clinic, Nov. 4, 2009, pp. 1-15.*

(Continued)

*Primary Examiner* — James Kish
(74) *Attorney, Agent, or Firm* — The Law Office of Patrick F. O'Reilly III, LLC (57) ABSTRACT

An integral laser imaging and coagulation apparatus, and associated systems and methods that allow an ophthalmologist to perform laser retinal surgical procedures with an integral laser imaging and coagulation apparatus disposed at a first (i.e. local) location from a control system disposed at a second (i.e. remote) location, e.g., a physician's office. In some embodiments, communication between the integral laser imaging and coagulation apparatus and control system is achieved via the Internet®.

20 Claims, 6 Drawing Sheets

(56) References Cited

U.S. PATENT DOCUMENTS

| | | |
|---|---|---|
| 5,943,116 A | 8/1999 | Zeimer |
| 5,993,001 A * | 11/1999 | Bursell et al. .................. 351/212 |
| 6,173,068 B1 | 1/2001 | Prokoski |
| 6,296,358 B1 | 10/2001 | Cornsweet et al. |
| 6,529,617 B1 * | 3/2003 | Prokoski ....................... 382/128 |
| 6,544,254 B1 | 4/2003 | Bath |
| 6,546,198 B2 | 4/2003 | Ohtsuka |
| 6,636,696 B2 | 10/2003 | Saito |
| 7,206,435 B2 | 4/2007 | Fujimura et al. |
| 7,206,626 B2 | 4/2007 | Quaid, III |
| 8,121,663 B2 | 2/2012 | Peyman et al. |
| 2003/0208189 A1 | 11/2003 | Payman |
| 2009/0240149 A1 * | 9/2009 | Peyman ......................... 600/439 |
| 2010/0060728 A1 | 3/2010 | Bublitz et al. |
| 2010/0245766 A1 * | 9/2010 | Zhang et al. .................. 351/206 |
| 2012/0150159 A1 * | 6/2012 | Kunath-Fandrei et al. ....... 606/4 |

OTHER PUBLICATIONS

Ertel et al., "Retinal Evaluation Efficacy of a Scanning Laser Opthalmoscope (Optos P200) Compared to a Digital Retinal Camera," White Rock Optometry Clinic, Nov. 4, 2009, pp. 1-15 (and p. 16 providing the earliest recorded date).

First office action on the merits (Non-Final Rejection) in U.S. Appl. No. 12/925,518, mailed on Mar. 7, 2012.

Second office action on the merits (Final Rejection) in U.S. Appl. No. 12/925,518, mailed on May 1, 2012.

Third office action on the merits (Non-Final Rejection) in U.S. Appl. No. 12/925,518, mailed on Dec. 5, 2012.

Fourth office action on the merits (Final Rejection) in U.S. Appl. No. 12/925,518, mailed on Mar. 21, 2013.

Notice of Allowance in U.S. Appl. No. 12/925,518, mailed on Apr. 12, 2013.

* cited by examiner

LASER COAGULATION OF AN EYE STRUCTURE FROM A REMOTE LOCATION

CROSS-REFERENCE TO RELATED APPLICATIONS

This application is a continuation-in-part of U.S. application Ser. No. 12/925,518 now U.S. Pat. No. 8,452,372, filed on Oct. 22, 2010 which claims the benefit of U.S. Provisional Application No. 61/455,111, filed Oct. 13, 2010.

FIELD OF THE INVENTION

The present invention relates to methods and systems for laser coagulation of the eye. More particularly, the present invention relates to non-invasive and non-contact methods and systems for laser coagulation of predetermined portions of the biological organism in the eye; particularly, the retina.

BACKGROUND OF THE INVENTION

As is well known in the art, various eye disorders, such as diabetic retinopathy, vascular occlusion, neovascularization and age macular degeneration, can, and in most instances will, have an adverse effect on the retina. Indeed, if not treated at the appropriate stage, noted diseases, particularly, diabetic retinopathy, can lead to severe losses in vision.

Various methods and systems have thus been developed to aid in the diagnosis of the noted eye diseases. The method often employed by eye care specialist, such as an ophthalmologist, is to examine the ocular fundus (the inside back surface of the eye containing the retina, blood vessels, nerve fibers, and other structures) with an ophthalmoscope.

The ophthalmoscope is a small, hand-held device, which, when appropriately positioned, shines light through a subject's pupil to illuminate to fundus. By properly focusing the light reflected from the subject's fundus, an examiner can observe the fundus structures.

As is well known in the art, examination of the ocular fundus can also be achieved using a fundus or slit lamp camera. Illustrative are the apparatus and systems disclosed in U.S. Pat. Nos. 5,713,047, 5,943,116, 5,572,266, 4,838,680, 6,546,198, 6,636,696, 4,247,176; 5,742,374 and 6,296,358.

Various method and systems have also been developed to treat eye disorders, such as diabetic retinopathy, glaucoma and age macular degeneration. One known method of treating the noted eye disorders, as well as retinal detachment, is laser coagulation of predetermined biological structures of the eye, such as the retina.

As is well known in the art, during laser coagulation of an eye structure, laser energy is transmitted to the structure to effect coagulation thereof. A typical laser coagulation system thus includes a laser energy or beam source, such as a beam projector, a slit image projector or lamp for forming a slit image on the eye, and observation equipment for observing the slit image and laser spot(s) in the eye. Illustrative are the laser coagulation systems disclosed in U.S. Pat. Nos. 4,759,360 and 4,736,744.

A major drawback associated with each of the noted conventional systems, as well as most known laser coagulation systems (and associated methods), is that the conventional slit lamp systems require a contact lens to neutralize the refractive power of the cornea. A contact lens is also necessary to provide a variable field of view of the retina up to 130°.

As is well known in the art, the contact lens must be appropriately positioned on the surface of the cornea and held at the desired position by the specialist, e.g., surgeon, while looking through the slit lamp microscope.

There are several drawbacks associated with the use of a contact lens during laser coagulation. A major drawback is that the use of a contact lens requires topical anesthesia and a dilated pupil for laser application. As is well known in the art, a contact lens can, and in many instances will, cause corneal abrasion on an anesthetized cornea.

A further drawback associated with conventional laser coagulation procedures is that the laser procedures are dependent on the steadiness of the physician's hands and the subject's head.

Another apparatus that is often used for laser energy delivery to the peripheral retina is the indirect ophthalmoscope. Use of the indirect ophthalmoscope requires a physician to hold an appropriate convex lens in front of the eye (pupil) with one hand to focus the laser beam on the retina, while the eye is indented with another hand to bring the peripheral retina into the field of view for laser application.

Although laser delivery with an indirect ophthalmoscope eliminates the need for a contact lens, there are still drawbacks and disadvantages associated with use of an indirect ophthalmoscope, A major drawback is that during laser delivery (and, hence, coagulation of a desired eye structure), the ophthalmoscope is often carried on the physician's head for 30-60 mins. This extended period causes extreme fatigue for the physician.

The indentation of the eye for the extended period is also very unpleasant for the subject or patient.

A further drawback associated with the use of an indirect ophthalmoscope for laser coagulation is that the indirect ophthalmoscope does not provide a retained record or documentation for future evaluation. Further, in most instances, the subject typically requires subsequent fundus photography.

It would thus be desirable to provide non-contact systems and methods for laser coagulation of eye structures to treat eye disorders It is therefore an object of the present invention to provide non-contact systems and methods for laser coagulation of eye structures that substantially reduce or overcome the noted drawbacks and disadvantages associated with conventional contact-based laser coagulation systems and methods.

It is another object of the present invention to provide non-contact apparatus, systems and methods for laser imaging and coagulation of an eye structure.

It is another object of the present invention to provide non-contact apparatus, systems and methods for laser imaging and coagulation of the retina and its periphery to treat retina and choroideal disorders and/or diseases.

SUMMARY OF THE INVENTION

The present invention is directed to laser imaging and coagulation apparatus, systems and methods that allow an eye specialist, e.g., an ophthalmologist or surgeon, to perform laser surgery on an eye structure, e.g. retina, with an integral laser imaging and coagulation apparatus disposed at a first (i.e. local) location from a control system disposed at a second (i.e. remote) location, e.g., a physician's office. The laser imaging and coagulation apparatus, systems and methods of the invention thus make it possible for an ophthalmologist to screen and perform laser surgery to treat various eye disorders, including, without limitation, diabetic retinopathy, vascular occlusion, neovascularization and age macular degeneration from a geographically remote location.

In one embodiment of the invention, the laser coagulation system includes (i) at least a first laser-imaging system disposed at a first location, the first laser-imaging system including a first laser-imaging apparatus, a photoaccoustic system, a first processor and a local control module, the first laser-imaging apparatus including a wide angle digital image acquisition system for acquiring digital images of a subject's eye structure and a laser generation system for transmitting an aiming laser beam and at least a first coagulation laser beam to said eye structure, the first coagulation laser beam having a first laser energy, the photoaccoustic system being configured to measure temperature of eye structure tissue subjected to said first laser energy, the local control module including local operation, local operation and performance simulation and local safety and verification sub-modules; and (ii) a central control system disposed at a remote site, the central control system including a second processor and a remote control module, the remote control module including remote operation, remote operation and performance simulation, and remote safety and verification sub-modules, the remote operations sub-module being configured to facilitate communications between a remote physician and the remote processor, and perform a laser coagulation procedure on the eye structure in an actual control mode.

In some embodiments of the invention, the local operation sub-module is configured to acquire at least a first eye structure image from the digital image acquisition system and transmit the first eye structure image to the remote site, receive a target laser transmission area and laser transmission parameters from a remote physician, apply an active contour algorithm to partition the first eye structure image into a grid map, perform a scatter laser (focal or grid) coagulation of the eye structure under the remote physician's command, acquire a plurality of post-procedure eye structure images, and transmit the post-procedure eye structure images to the remote site for evaluation and verification of treatment.

In some embodiments, the remote operations sub-module is further configured to execute a virtual treatment of the eye structure and perform a test surgical procedure in association with the local operation and performance simulation sub-module.

In some embodiments, the remote operation and performance simulation sub-module is configured to test performance parameters of the local operation module and perform virtual treatment of the eye structure by the remote physician.

In some embodiments of the invention, the photoaccoustic system is configured to control the laser generation system.

In one embodiment of the invention, the eye structure comprises the retina.

In some embodiments of the invention, the laser coagulation system also includes eye tracking means for tracking movement of the eye.

In some embodiments of the invention, the laser coagulation system also includes facial recognition means for identifying and/or verifying the identity of the subject.

In one embodiment, communication by and between the central control system and the laser-imaging apparatus is achieved via the Internet®

BRIEF DESCRIPTION OF THE DRAWINGS

Further features and advantages will become apparent from the following and more particular description of the preferred embodiments of the invention, as illustrated in the accompanying drawings, and in which like referenced characters generally refer to the same parts or elements throughout the views, and in which.

DETAILED DESCRIPTION OF THE PREFERRED EMBODIMENT

Before describing the present invention in detail, it is to be understood that this invention is not limited to particularly exemplified apparatus, systems, structures or methods as such may, of course, vary. Thus, although a number of apparatus, systems and methods similar or equivalent to those described herein can be used in the practice of the present invention, the preferred apparatus, systems, structures and methods are described herein.

It is also to be understood that the terminology used herein is for the purpose of describing particular embodiments of the invention only and is not intended to be limiting.

Unless defined otherwise, all technical and scientific terms used herein have the same meaning as commonly understood by one having ordinary skill in the art to which the invention pertains.

Further, all publications, patents and patent applications cited herein, whether supra or infra, are hereby incorporated by reference in their entirety.

Finally, as used in this specification and the appended claims, the singular forms "a, "an" and "the" include plural referents unless the content clearly dictates otherwise. Thus, for example, reference to "a laser image" includes two or more such images and the like.

DEFINITIONS

The terms "eye disorder" and "eye disease" are used interchangeably herein and mean and include, without limitation, diabetic retinopathy, vascular occlusion, neovascularization, retinal detachment, neoplastic tissue, ischemic retina, retinopathy of prematurity and age related macular degeneration.

The following disclosure is provided to further explain an enabling fashion the best modes of performing one or more embodiments of the present invention. The disclosure is further offered to enhance an understanding and appreciation for the inventive principles and advantages thereof, rather than to limit in any manner the invention. The invention is defined solely by the appended claims including any amendments made during the pendency of this application and all equivalents of those claims as issued.

As will readily be appreciated by one having ordinary skill in the art, the present invention substantially reduces or eliminates the disadvantages and drawbacks associated with conventional systems and methods for coagulating eye structures to treat eye disorders.

In overview, the present disclosure is directed to laser imaging and coagulation apparatus, systems and methods that allow an eye specialist, e.g., an ophthalmologist or surgeon, to perform laser retinal surgical procedures, such as laser or tissue coagulation, with an integral laser imaging and coagulation apparatus disposed at a first (i.e. local) location from a control system disposed at a second (i.e. remote) location, e.g., a physician's office.

By the term "laser coagulation", as used herein, it is meant to mean and include, without limitation, selective absorbance of transmitted light energy (having a visible green wavelength) by hemoglobin in biological tissue and, hence, sealing of blood vessels in the tissue. In a preferred embodiment of the invention, the wavelength of the transmitted energy (referred to herein as a "treatment or coagulative laser beam") is in the range of approximately 400-1650 nm, more preferably, in the range of approximately 530-670 nm.

Although the present invention is directed to thermotherapy of biological tissue by laser energy, it is to be understood the invention is not limited to such form of energy. Indeed, as will readily be appreciated by one having ordinary skill in the art, the thermotherapy of biological tissue described herein, i.e. coagulation of selective eye structures, can also be achieved via the application of electromagnetic radiation, and radio frequency and ultrasound energy.

It is further to be understood that, although the biological tissue subject to the thermotherapy (i.e. coagulation), in accordance with the present invention, comprises the retina, the invention is not limited solely to thermotherapy of the retina. According to the invention, the thermotherapy of the present invention can be employed to coagulate any eye structure.

The laser-imaging apparatus, systems and methods of the invention, and laser energy transmitted thereby, can thus be employed to treat various eye disorders, including, without limitation, diabetic retinopathy, vascular occlusion, neovascularization, retinal detachment, neoplastic tissue, ischemic retina, retinopathy of prematurity and age related macular degeneration.

The laser-imaging apparatus, systems and methods of the invention, and laser energy transmitted thereby, can also be readily employed in refractive surgical procedures to, for example, perform corneal surface ablation using an eximer or femtosecond laser, LASIK procedures, and/or lid surface and surrounding tissue tightening using an infrared laser.

The laser-imaging apparatus, systems and methods of the invention, and laser energy transmitted thereby, can also be readily employed in cosmetic surgical procedures to, for example, remove skin lesions and perform skin resurfacing.

Figure 1:
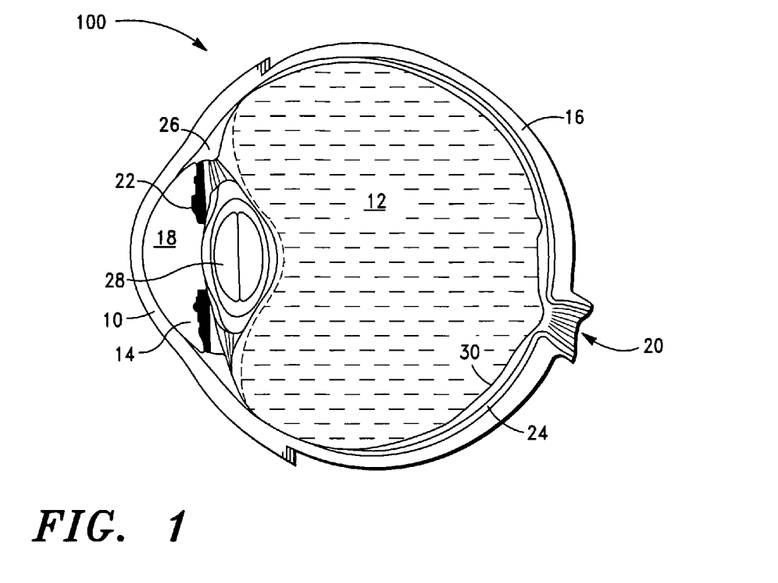
FIG. 1 is an illustration of a human eye showing the major structures thereof.

Before describing the invention in detail, the following brief description of the various anatomical features of the eye is provided, which will help in the understanding of the various features of the invention:

Referring to FIG. 1, the cornea 10, which is the transparent window that covers the front of the eye 100, is a lens-like structure that provides two-thirds of the focusing power of the eye.

The cornea 10 is slightly oval, having an average diameter of about 12 mm horizontally and 11 mm vertically. The central thickness of the cornea 10 is approximately 550 μm.

The sclera 16 is the white region of the eye, i.e. posterior five sixths of the globe. It is the tough, avascular, outer fibrous layer of the eye that forms a protective envelope. The sclera is mostly composed of dense collagen fibrils that are irregular in size and arrangement (as opposed to the cornea). The extraocular muscles insert into the sclera behind the limbus.

The sclera 16 can be subdivided into 3 layers: the episclera, sclera proper and lamina fusca. The episclera is the most expernal layer. It is a loose connective tissue adjacent to the periorbital fat and is well vascularized.

The sclera proper, also called tenon's capsule, is the layer that gives the eye 100 its toughness. The sclera proper is avascular and composed of dense type I and III collagen.

The lamina fusca is the inner aspect of the sclera 16. It is located adjacent to the choroid and contains thin collagen fibers and pigment cells.

The pars plana is a discrete area of the sclera 16. This area is a virtually concentric ring that is located between 2 mm and 4 mm away from the cornea 10.

The vitreous humor or vitreous 12 is the largest chamber of the eye 100 (i.e. ~4.5 ml). The vitreous 12 is a viscous transparent gel composed mostly of water. Unlike the fluid contained in the frontal parts of the eye (e.g., aqueous humor, discussed below), which are continuously replenished, the transparent gel in the vitreous chamber is stagnant.

As is well known in the art, the vitreous humor 12 also contains a random network of thin collagen fibers, mucopolysaccharides and hyaluronic acid.

The aqueous humor 14 occupies the anterior chamber 18 of the eye 100. The aqueous humor 14 has a volume of about 0.6 mL and provides nutrients to the cornea 10 and lens 28.

One of the most important functions of the aqueous humor 14 is to maintain IOP by the rate of its production and drainage.

The additional parts of the eye that are illustrated in FIG. 1 comprise the uvea, and structures thereof, lens 28 and retina 30.

The uvea refers to the pigmented layer of the eye 100 and is made up of three distinct structures: the iris 22, ciliary body, and choroid 24. The iris 22 is the annular skirt of tissue in the anterior chamber 18 that functions as an aperture. The pupil is the central opening in the iris 22.

The ciliary body is the 6 mm portion of uvea between the iris 22 and choroid 24. The ciliary body is attached to the sclera 16 at the scleral spur. It is composed of two zones: the anterior 2 mm pars plicata, which contains the ciliary muscle 26, vessels, and processes, and the posterior 4 mm pars plana.

The ciliary muscle 26 controls accommodation (focusing) of the lens 28, while the ciliary processes suspend the lens 28 (from small fibers, i.e. zonules) and produce the aqueous humor 14 (the fluid that fills the anterior and posterior chambers and maintains intraocular pressure).

The choroid 24 is the tissue disposed between the sclera 16 and retina 30. The choroid 24 is attached to the sclera 16 at the optic nerve and scleral spur. This highly vascular tissue supplies nutrients to the retinal pigment epithelium (RPE) and outer retinal layers.

The layers of the choroid 24 (from inner to outer) include the Bruch's membrane, choriocapillaris and stroma. Bruch's membrane separates the RPE from the choroid 24 and is a permeable layer composed of the basement membrane of each, with collagen and elastic tissues in the middle.

The crystalline lens 28, located between the posterior chamber and the vitreous cavity, separates the anterior and posterior segments of the eye 100. Zonular fibers suspend the lens from the ciliary body and enable the ciliary muscle to focus the lens 28 by changing its shape.

The retina 30 is the delicate transparent light sensing inner layer of the eye 100. The retina 30 faces the vitreous and consists of two basic layers: the neural retina and retinal pigment epithelium. The neural retina is the inner layer. The retinal pigment epithelium is the outer layer that rests on Bruch's membrane and choroid 24.

As indicated above, conventional slit lamp systems, which are often employed to treat various eye disorders, such as diabetic retinopathy, require a contact lens to neutralize the refractive power of the cornea and to provide a variable field of view of the retina.

The length of time to perform a surgical procedure with a conventional slit lamp system is also presently in the range of 30 minutes to an hour. There is thus an increased percentage of probable error due to the laser photo-coagulation being controlled manually, i.e. by the physician's hand, and the potential eye movements from the patient during this extended period of time.

The present invention substantially reduces or eliminates the disadvantages and drawbacks associated with conventional slit lamp systems and associated methods. As discussed in detail herein, the laser-imaging apparatus include means for taking and storing digital images of the target eye structure (s), which can be retrieved on a monitor for diagnosis and defining the area of treatment. In some embodiments, the laser-imaging apparatus (and systems) of the invention thus include a retinal camera (e.g., Topcon, Zeiss, Kowa or preferably a wide angle viewing system having an elliptical mirror), which, in some embodiments, is modified with a wide-angle lens.

A wide field scanning laser-imaging apparatus, such as the laser opthalmoscope disclosed in U.S. Pat. No. 5,815,242, can also be employed to provide images of the fundus, particularly, the retina. The noted laser-imaging apparatus can also be readily modified for laser coagulation procedures in one or multiple health care applications or additional vision care offices.

According to the invention, the viewing light can comprise a white light from a flush light, laser source or one or more scanning lasers with compensatory wavelengths in the range of approximately 190 nm-10,000 nm, more preferably, in the range of approximately 400-1060 nm, to obtain a fundus photograph.

According to the invention, the retinal camera is connected to laser transmission means (or a laser system) that is adapted to generate and transmit laser energy that is sufficient to coagulate any desired portion of the retina using a monitor's touch screen.

In a preferred embodiment of the invention, the laser-imaging apparatus incorporates aiming and treatment laser generating and transmission means into an existing camera (e.g., Topcon, Zeiss, etc.) or a wide angle viewing system/camera, such as the laser opthalmoscope disclosed in U.S. Pat. No. 5,815,242. The laser-imaging apparatus also includes control means for controlling the aiming and treatment laser means, and the camera.

Preferably, the transmitted laser beam passes through the optical path of the viewing apparatus (or system) and is preferably reflected off of an elliptical mirror in the camera (in which the imaging light is focused toward the pupil or slightly behind the pupil), providing a field of view greater than approximately 200°.

Figure 2:
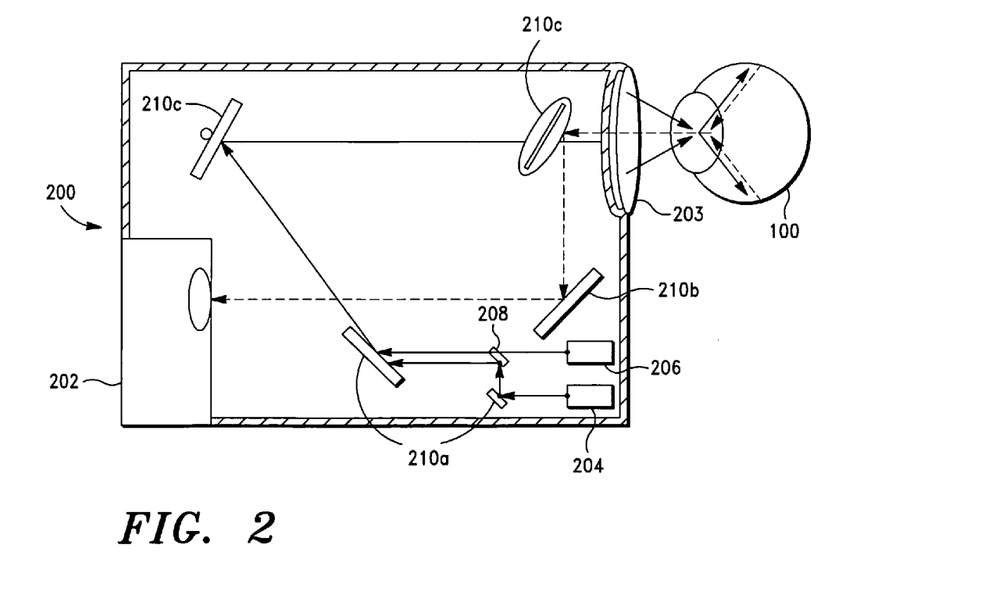
FIG. 2 is a schematic illustration of one embodiment of a laser-imaging apparatus, in accordance with the invention.

Referring now to FIG. 2, there is shown one embodiment of a laser-imaging apparatus of the invention. As illustrated in FIG. 2, the laser-imaging apparatus 200 includes a Topcon digital camera 202, scanning laser visualization means 204 and internal laser generation and transmission means (i.e. coagulation means) 206. The laser-imaging apparatus 200 further includes a refracting lens 203, at least one two-way mirror 208 and a plurality of appropriately positioned reflecting mirrors 201a-201c.

Figure 3:
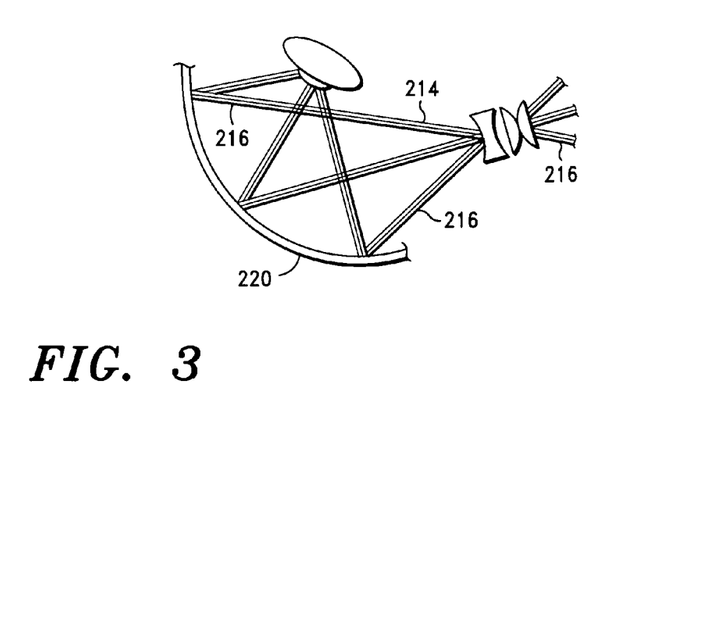
FIG. 3 is a schematic illustration of another embodiment of a laser-imaging apparatus, showing the elliptical mirror thereof, in accordance with the invention.

Referring now to FIG. 3, in an alternative embodiment, a wide angle camera equipped with an elliptical mirror 220 is employed. According to the invention, the illustrated wide angle camera provides an improved range of 150-200° of the retina for optimal treatment.

FIG. 3 shows the path of the viewing/imaging scanning laser beams 214 as they are reflected and pass through the focal point of the mirror behind the pupil (Black) toward the retina. As illustrated in FIG. 3, the coagulative laser beam 216 preferably passes through the same path as the viewing/imaging beams 214.

In some embodiments of the invention, the laser-imaging apparatus of the invention also includes an optical coherence tomography (OCT) means.

Preferably, the rays reflected back from the retina pass through the same pathway and form a digital image that can be observed on the monitor.

According to the invention, the coagulative laser beam is also scanned over the retinal area via the same light path as used for the observation and documentation.

The integration of the aiming and treatment laser generating and transmission means with a camera requires the introduction of precision motorized optical fixtures. An opto-mechanical system having an integral control system is thus provided to control and/or position the target spot of the laser beam(s) in x and y directions within the eye. The system is designed and adapted to interface with joystick commands and/or computer/monitor touch screen commands, for local and remote control of the aiming and treatment (or coagulative) laser transmissions, respectively.

In some embodiments of the invention, the control means for positioning the laser transmissions (or beams) within the eye consists of two main components. The first component is adapted to move the beams in the x-direction. The second component is adapted to move the beams in the y-direction.

Preferably, movement in the y-direction is provided by a mirrored surface disposed in the optical path of the camera. This y-direction, motorized fixture provides precise movement of the mirrored surface, while still allowing diagnostic and treatment images to be seen through the retinal camera.

In some embodiments of the invention, producing the x-direction movement involves physically moving the laser unit; the movement of the laser being either translational or rotational. Various conventional means of motorized movement can also be employed to provide movement in the x-direction.

In a preferred embodiment, the laser-imaging apparatus is in communication with another remote system via the Internet®, whereby the laser-imaging apparatus can be controlled by a physician at the remote site (e.g., medical center).

According to the invention, location of laser energy or beam application can be from 5-200° of the retina. In some embodiments, location of laser energy application is preferably 30-200° of the retina.

In some embodiments of the invention, the transmitted coagulative laser energy (or beam(s)) has a wavelength in the range of approximately 400-1650 nm, more preferably, in the range of approximately 530-670 nm. The laser (or laser energy) can also be transmitted in a pulsed manner or continuously.

According to the invention, the laser spot size can be in the range of approximately 10 micron-1500 micron.

According to the invention, exposure time of the laser energy application can be in the range of approximately 1 femto-seconds to 1000 seconds.

In some embodiments of the invention, the laser-imaging apparatus 200 includes a photoaccoustic system that can measure the temperature inside the eye tissue during and after laser scanning. A preferred photoaccoustic system is disclosed in Applicant's U.S. Pat. No. 8,121,663; which is incorporated by reference herein in its entirety.

As set forth in detail in the '663 patent, the photoaccoustic system is adapted to record the sonic waves that are generated by heating eye tissue, e.g. retina tissue. This provides precise information of the temperature generated as a result of the laser transmission, i.e. coagulative laser energy.

Figure 4:
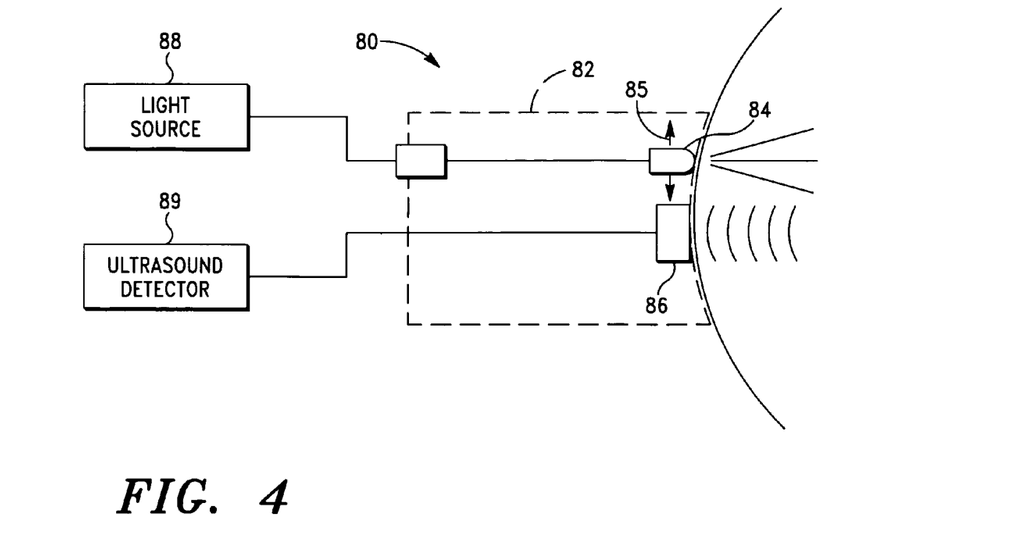
FIG. 4 is a schematic illustration of a photoaccoustic system, in accordance with the invention.

Referring now to FIG. 4, there is shown one embodiment of a photoaccoustic system 80. As illustrated in FIG. 4, the photoaccoustic system 80 includes a laser source 88, an ultrasonic detector 89, and a probe module 82. The probe module 82 includes an objective lens structure 84, which is preferably coupled to the light source 88 via a fiber optic connection or other light transmitter. Alternatively, the light source can be incorporated into the probe module 82.

According to the invention, the light source 88 can comprise a laser, laser diode or superluminescent diode (SLD), as appropriate for generating the desired light wavelength and intensity. The light can also be delivered as pulses or as modulated radiation.

As further illustrated in FIG. 4, the probe module 82 further contains an ultrasound transducer 86 that is adapted to detect the photoaccoustic waves that are generated as a result of the absorption of energy from the light emitted by the objective lens structure 84. The ultrasound transducer 86 is in contact with the eye 100 or an eyelid drawn over the eye.

As light is delivered as pulses or as modulated radiation, pulses or modulating acoustic signals are generated and returned to the ultrasound transducer 86 in probe module 82.

According to the invention, localization of the source of photoaccoustic signals can be achieved in various manners. First, localization can be accomplished by directing the beam from objective lens structure 84 in specific directions, by moving that structure with micromechanical actuators, as shown diagrammatically at 85 in FIG. 4, thus targeting a particular line of points in the eye.

Furthermore, by suitable optics included in objective lens structure 84, the focal point of the emitted light may be moved within the eye to a desired point, such as a point along the retina vasculature, to selectively generate acoustic signals at that desired point. Because the eye is optically transmissive relative to soft tissue, beam focusing and beam directing are likely to be more accurately performed in the eye, than is the case is soft tissue elsewhere in the body.

To further assist in directionally capturing the photoaccoustic signals generated within the eye, a directional transducer array can be used as transducer 86, to control the directionality of reception of ultrasonic energy, thus further localizing upon a desired source of thermoacoustic signals. Thus, by targeting the focal point of the illuminating light, and also directionally targeting the reception of ultrasonic signals by the transducer array, thermoacoustic signals from a particular location, such as along the retina, may be specifically targeted.

Overview of Laser-Imaging System

Figure 5:
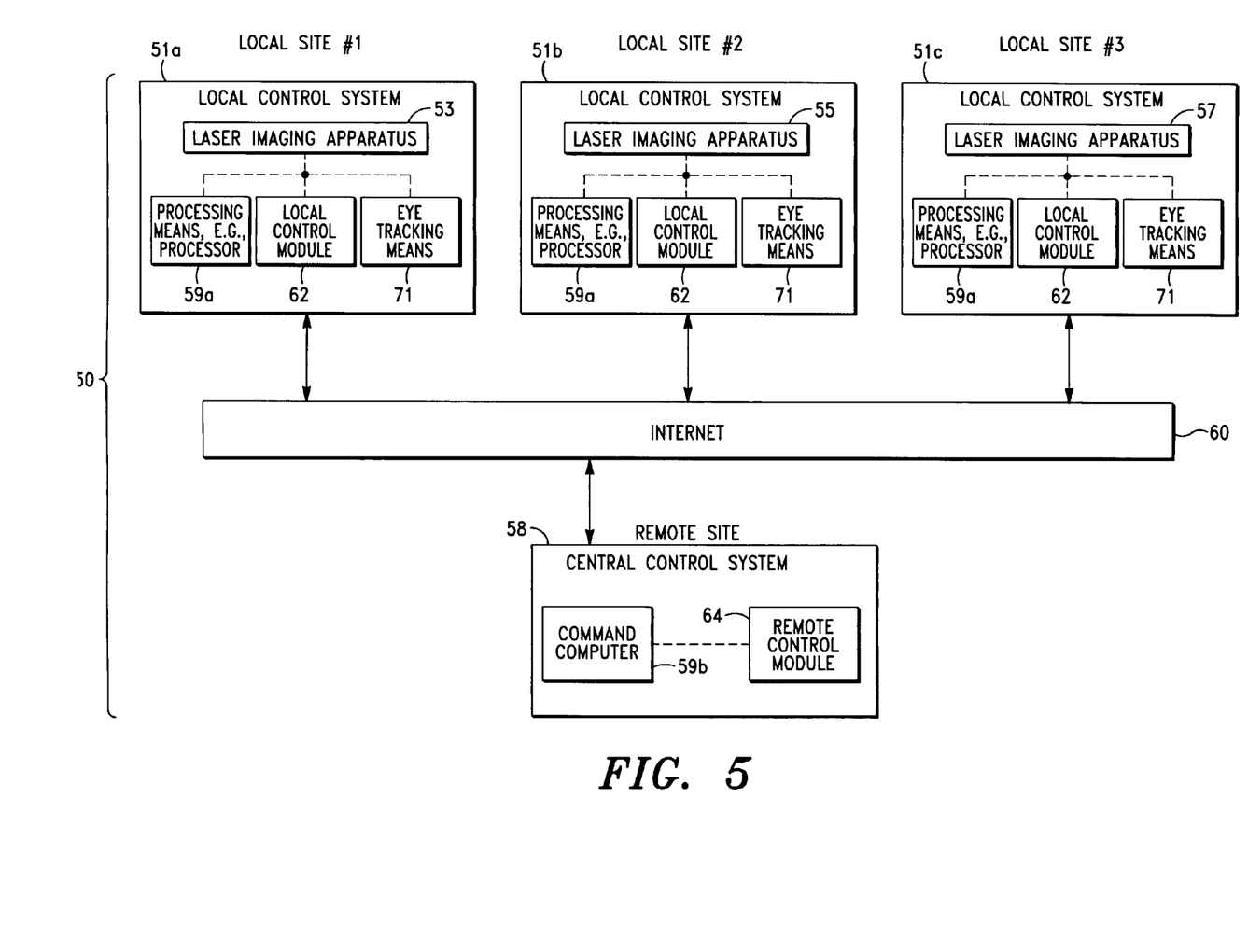
FIG. 5 is a schematic illustration of one embodiment of a laser-imaging system, in accordance with the invention.

Referring now to FIG. 5, there is shown a schematic diagram of a laser-imaging system 50, according to one embodiment of the invention. As illustrated in FIG. 5, the system 50 includes at least one, preferably, multiple local systems 52, 54, 56 disposed at local sites 51a, 51b, 51c; each system 52, 54, 56 including a laser-imaging apparatus (denoted "53", "55" and "57"), such as the apparatus 200 shown in FIG. 2. In a preferred embodiment of the invention, each laser-imaging apparatus 53, 55, 57 includes a photoaccoustic system, such as system 80 discussed above.

Preferably, each laser-imaging apparatus 53, 55, 57 is preferably in communication with a local control module 62 and control-processing means 59a, such as a personal computer.

In some embodiments of the invention, at least the control-processing means 59a disposed at each local site 51a, 51b, 51c includes facial recognition means for identifying and/or verifying the identity of a subject or patient. Alternatively, in some embodiments, the control-processing means 59b disposed at the remote site 51d (discussed below) includes facial recognition means. In some embodiments both control-processing means 59a, 59b include facial recognition means.

In some embodiments of the invention, each local system 52, 54, 56 also includes eye tracking means for measuring eye position(s) and movement. According to the invention, the eye tracking means can be an integral component or feature of the laser-imaging apparatus 53, 55, 57 or a separate system or device.

Also disposed at each local site 51a, 51b, 51c during a laser procedure is a test subject or patient and a physician or technician.

As also illustrated in FIG. 4, the system 50 also includes a remote site 58 having a command computer 59 that is operatively connected to a remote control module 64. Also disposed at the remote site 58 during a laser procedure is a system operator (e.g., retinal surgeon).

As discussed in detail below, communication by and between the local sites 52, 54, 56 and the remote site 58 is preferably facilitated by the local and remote control modules 62, 64 and the Internet® 60.

In accordance with one embodiment of the invention, the sequence of interactions between the local sites 52, 54, 56 and remote site 58 comprises the following:

Fundus photograph is digitally transmitted to remote site;
Image is acquired by remote site and filed in the computer at remote site;
Eye is repositioned in front of the camera, fundus image is taken for pattern recognition and tracking, and transmitted to remote site, verified as matching previous, pre-existing image on file;
New image is selected and employed as simulator;
Spot size, power level, and time interval between each laser is chosen;
Tracking system (fail-safe) is checked;
Fundus laser treatment is performed in virtual mode to establish the desired laser coagulation; and
After choosing spot size and duration of laser application, power is adjusted to the lowest increment of energy that may or may not be able to create a response on the patient's eye. The power of the laser is incrementally increased until the test spot demonstrates the desired effect.

In a preferred embodiment, the optimum power and, hence, temperature required for a procedure is provided via the photoaccoustic system. The photoaccoustic system is further adapted to maintain the transmitted laser energy at a fixed, pre-selected level. This particularly results in a uniform coagulation of the retina.

Local and Remote Control Modules

Figure 6:
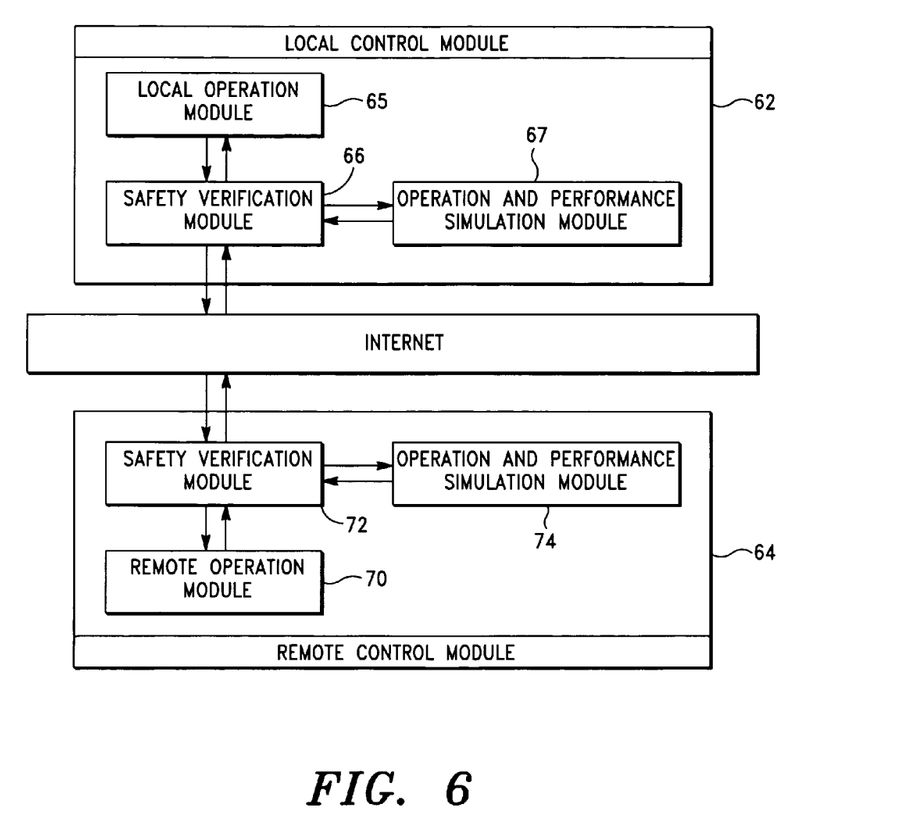
FIG. 6 is another schematic illustration of the laser-imaging system shown in FIG. 5, showing the local and remote modules thereof, in accordance with one embodiment of the invention.

Referring now to FIG. 6, there is shown a schematic diagram of a local control module 62 and a remote control module 64, according to one embodiment of the invention. As illustrated in FIG. 6, the local control module 62 preferably includes three sub-modules: an operation module 65, safety and verification module 66, and an operation and performance simulation module 67.

The remote control module 64 similarly includes three sub-modules: an operation module 70, safety and verification module 72, and an operation and performance simulation module 74.

Each of these sub-modules 65, 66, 67 is described below.

Local Operation Module

According to the invention, the local operation module 65 provides a local technician with an interface to a personal computer for data acquisition and eye treatment.

Figure 10:
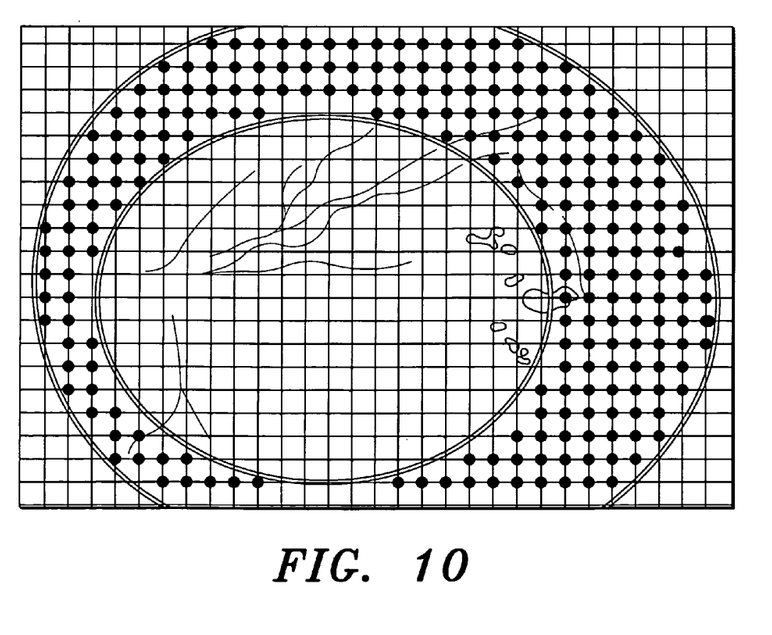
FIG. 10 is an illustration of a human retina, showing a generated grid map on the retina, in accordance with one embodiment of the invention.

According to the invention, the major tasks performed by the local operation module 65 include the following:

(1) acquiring a plurality (preferably, in the range of 5-7) standard fields of the fundus retinal images and transmission of the images to the remote site 58;

(2) receiving the oval area encompassing the focused region of the retina outlined by the remote physician (see FIG. 5), as well as parameters for the spot size, power and duration of laser application;

(3) applying a snake algorithm (i.e. active contour algorithm) to extract the contours, calculating the corresponding areas between the contours, and partitioning the image into a grid map (see FIG. 10), as a function of the specified surgical area and corresponding parameters for laser application from the remote center. According to the invention, the resolution of the grid is adjusted according the area between the contours, whereby the number of nodes between the contours (i.e. the black points between the two white contours) is large enough to generate in the range of approximately 700-1000 laser sports to ensure the surgery precision;

(4) performing the scatter laser coagulation under the remote doctor's command. During the process (which is performed in real-time), the Kalman filter and mean shift algorithm are preferably integrated to detect and estimate the test subject's eye moment: a) if the movement is under the given safety threshold, the laser system will be adjusted using a simple PID control algorithm based on the estimated motion so that it will be focused on the remotely specified spot within allowable, surgical accuracy, and then the laser will be applied; b) if the estimated movement is beyond the specified safety threshold, the laser coagulation procedure will be terminated immediately and a warning message will be transmitted to the remote control module 64. Step (1), above, will also be repeated until a stop instruction is received from the remote physician; and (5) acquiring a plurality (preferably, in the range of 4-5) standard fields of fundus retinal images and transmitting the images to the remote site for evaluation and verification of treatment.

Local Operation and Performance Simulation Module

According to the invention, the local operation and performance simulation module 67 allows the physician (or technician) to test the entire system 50 (e.g., tracking and interruption functions in the local operation module 65; communications between local and remote sites; safety and verification modules 66, 72 at both remote and local sites) before the system 50 is run in an actual control mode.

In the simulation mode, the local simulation module 67 replaces the test subject, but all the other modules (e.g., modules at the remote site 70, 72, 74; safety and verification module 66 and local operation module 65 at the local site) preferably operate in exactly the same manner.

Remote Operations Module

According to the invention, the remote operation module 70 provides the physician with an interface to a personal computer. During a laser procedure, some of the important tasks that the physician will perform (and are facilitated by the remote operation module) include: (1) screening via digitized photos, (2) outlining an oval area encompassing the center part of the retina (see FIG. 5), (3) choosing the spot size and duration of laser application, (4) adjusting the power via single shots of test spots (preferably, with a duration in the range of approximately 0.001-0.1 seconds in approximately 0.06 intervals), (5) executing virtual treatment with the simulation module (see FIG. 6), (6) performing a test surgery, which involves the local operation and performance simulation module 67, and (7) performing the laser surgery in the actual control mode (and observing the surgery via a real-time video stream).

Figure 7:
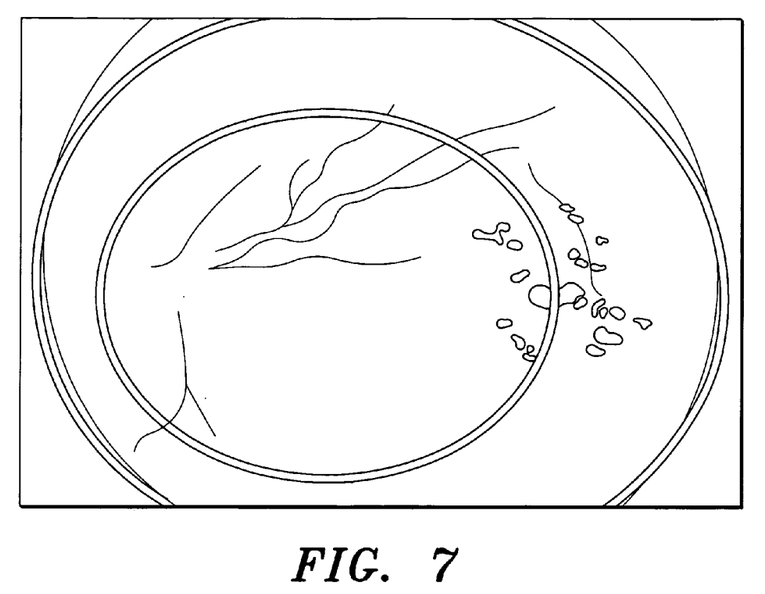
FIG. 7 is an illustration of a human retina, showing an oval area encompassing the target area on the retina for laser transmission, in accordance with one embodiment of the invention.
Figure 8:
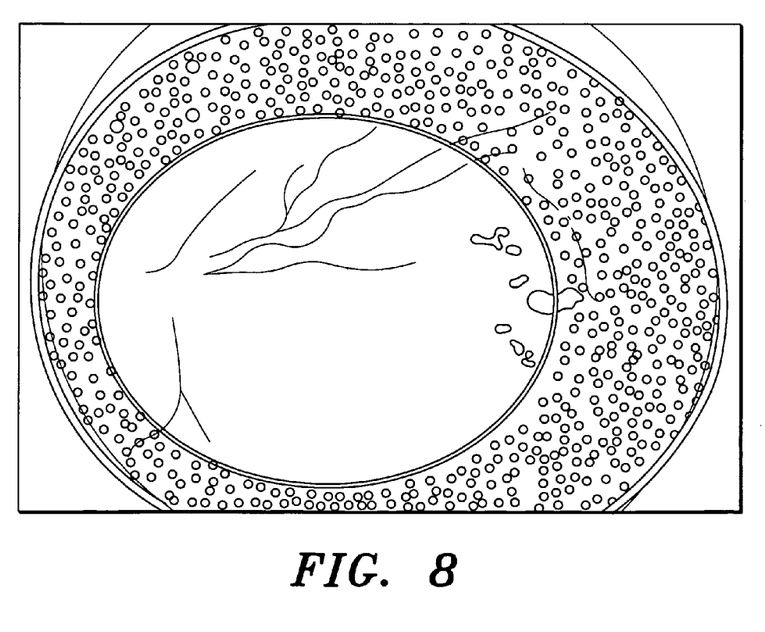
FIG. 8 is an illustration of a human retina, showing the distribution of laser spots resulting from a virtual treatment of the retina, in accordance with one embodiment of the invention.

Referring now to FIGS. 7 and 8 there are shown photographs of the retina, showing the outline of the oval target area (area bound by two oval lines) thereon for application of laser spots (FIG. 7) and the laser spots (in some embodiments, in the range of approximately 50-3000 laser spots) on the retina achieved via virtual treatment (see FIG. 8), as described below.

Remote Operation and Performance Simulation Module

According to the invention, the remote operation and performance simulation module 74 allows a physician or technician to perform virtual treatment, which permits the physician to test the local operation module 65 (at a local site) in terms of its generation capability of the laser spots throughout the surgery area specified by the doctor (see FIG. 8). The algorithm used in this simulation module is similar to the one used by the local operation module 65.

Figure 9:
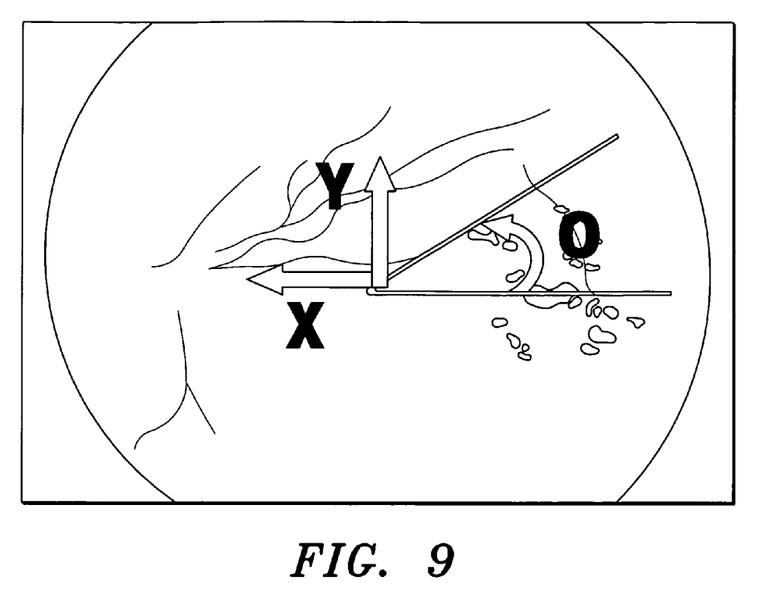
FIG. 9 is an illustration of a human retina, showing simulation variables associated with movement of the eye, in accordance with one embodiment of the invention.

Referring now to FIG. 9, in some embodiments, movement of the object (i.e. fundus photograph) is simulated via three random variables; X, Y and O. The variables X and Y denote the displacement changes in the X and Y axes, respectively. The variable O denotes the orientation changes.

To this end, movement data from test subjects is first collected, from which best-fit statistical distributions (and variances) for the three random variables (X, Y, and O) are determined. According to the invention, a "goodness-of-fit" test can then be performed to test the validity of the distribution.

If a theoretical distribution (involving larger p-value in statistical sense) exists, it will then be employed. Otherwise, an empirical distribution will be constructed and employed.

According to the invention, the remote operation and performance simulation module 74 also allows the physician to test the local operation module 67 (at a local site) in terms of its generation capability of the laser spots without involving communications with the local control module 62.

Safety and Verification Modules

According to the invention, safety and verification modules 66, 72 exist both at the remote site 58 as well as each local site 52, 54, 56 to ensure safe and effective operation of the system 50. In a preferred embodiment of the invention, several constraints are preferably imposed into the system 50 (both hardware and software). In some embodiments, the constraints include (1) physical constraints, (2) logical constraints, and (3) medical constraints.

According to the invention, physical constraints ensure various parameters or values (e.g., therapy beam power) in the laser system 50 are within a permitted range. If any of the values are outside a permitted range, laser firing will be automatically locked and notification of the unacceptable value(s) is transmitted to the physician at the remote site, as well as the technician at the local site.

Logical constraints are employed to ensure that a correct sequence of operational tasks is performed. For example, if a physician at a remote site mistakenly commands 700-1000 laser spots of laser application to the fundus before simulating the laser application in a simulation mode, the system will not execute the command and transmits a warning message to the physician. In a preferred embodiment, Unified Modeling Language (UML) is incorporated into the system software and employed to specify the logical constraints.

The medical constraints involve monitoring of the fundus of the test subject(s) during the actual laser procedure operation. If it is detected that the laser energy effect on the fundus is different from what the physician expected or the laser energy is applied beyond the specified area, laser energy transmission is immediately terminated. Notification of the issue is also transmitted to the physician at the remote site, as well as the physician or technician at the local site.

As indicated above, in some embodiments of the invention, the system 50 also includes eye tracking and facial recognition means to ensure safe operation.

System Software Platform

The software system that is employed to control the laser procedure(s) with the laser-imaging systems of the invention includes client/server architecture and a TCP/IP communication protocol. The client/server architecture comprises a computer science paradigm, where clients and servers are deemed separate software processes that can run on the same or different computers.

In some embodiments, the software recognizes the computer at the surgeon's site as a client, while the local control module at the remote patient's site is recognized as a server.

According to the invention, communication by and between the remote control module 64 and the local control module 62 is facilitated via web services implemented in .NET remoting technology.

When a physician at a remote site sends a control or data acquisition command, the command is first transmitted to the local control module 62 (or server) through the .NET remoting interface. In response to the command, the local control module 62 controls hardware compartments through a hardware specific interface (e.g., RS-232C interface, parallel communication protocol).

The communication speed between the client and the server will depend on several factors such as 1) the distances between the client and the server, 2) network traffic conditions, and 3) the size of data (e.g., images) being transmitted.

As will readily be appreciated by one having ordinary skill in the art, the present invention provides numerous advantages compared to prior art methods and systems for laser coagulation procedures. Among the advantages are the following:

The provision of laser-imaging systems, which will significantly reduce laser transmission and, hence, procedure time. For example, the length of time for the laser photocoagulation treatment for diabetic retinopathy will be reduced from 30-60 minutes per procedure to only two minutes.

The provision of laser-imaging systems, which will also reduce the probability of error associated with manual surgery (tremors and misjudgments) via a more precise computerized control mechanism, with additional fail-safe features, and a wider angle imaging camera for retina diseases. This offers more choices for various lasers with different wavelengths, intensities, and action than was previously possible.

The provision of laser-imaging systems, which will also allow a physician or surgeon to perform a procedure at a remote site, via a high-speed reliable Internet® connection, thus eliminating the need for the patient to travel a long distance to be treated at a specialist's office or, in the case of military field care or space exploration units, allowing patients to be treated immediately on-site.

The cameras employed in the systems can also be equipped with appropriate diode lasers and filters for auto-fluorescence photography and angiography of the retina.

One can also develop a miniature version of the system by using printing technology, such as inkjet, to generate and integrate the micro-optical parts not only on hard substrates, but also on those that are flexible. Having a miniature or micro-system will allow further use of such technology in hard to reach places.

Without departing from the spirit and scope of this invention, one of ordinary skill can make various changes and modifications to the invention to adapt it to various usages and conditions. As such, these changes and modifications are properly, equitably, and intended to be, within the full range of equivalence of the following claims.

What is claimed is:

1. A system for laser coagulation of an eye structure, comprising:
   a local control system disposed at a first location and a central control system disposed at a remote site, said remote site being at a second location,
   at least a first laser-imaging system disposed at said first location, said first laser-imaging system including a first laser-imaging apparatus, a laser generation system, a photoacoustic system, a first processor and a local control module,
   said first laser-imaging apparatus including a wide angle digital image acquisition system with at least one retinal viewing camera configured to acquire digital images of said eye structure, said local control module including local operation, local operation and performance simulation, and local safety and verification sub-modules;
   a laser generation system including an aiming laser configured to generate and transmit an aiming laser beam to said eye structure, and a treatment laser configured to generate and transmit at least a first coagulation laser beam to said eye structure, said first coagulation laser beam having a first laser energy;
   said local operation sub-module including a first computer configured and arranged to acquire at least a first eye structure image from said digital image acquisition system and transmit said first eye structure image to said remote site via a computer network, receive a target laser transmission area and laser transmission parameters from a remote physician via said computer network, apply an active contour algorithm to partition said first eye structure image into a grid map, execute a scatter laser coagulation of said eye structure using said treatment laser, acquire a plurality of post-procedure eye structure images, and transmit said post-procedure eye structure images to said remote site for evaluation and verification of treatment;
   said photoacoustic system including an ultrasound transducer configured to detect acoustic waves that are generated as a result of the absorption of energy by said eye structure such that said photoacoustic system is able to determine a temperature of said eye structure tissue subjected to said first laser energy, said ultrasound transducer comprising a transducer array configured to directionally target a reception of said acoustic waves; and said central control system including a second processor and a remote control module, said remote control module including remote operation, remote operation and performance simulation, and remote safety and verification sub-modules, said remote operations sub-module comprising a second computer configured and arranged to execute remote commands during a laser coagulation procedure on said eye structure in an actual control mode, wherein, in said actual control mode, said treatment laser is configured to transmit said first coagulation laser beam to said eye structure.

2. The system of claim 1, wherein said at least one retinal viewing camera of said digital image acquisition system provides a field of view of said eye structure between 150° and 200°.

3. The system of claim 1, wherein said digital image acquisition system further includes means for transmitting digital images of said eye structure to said local control module.

4. The system of claim 1, wherein said second computer of said remote operations sub-module is further configured to execute a virtual treatment of said eye structure and perform a test surgical procedure in association with said local operation and performance simulation sub-module.

5. The system of claim 1, wherein said treatment laser of said laser generation system is controlled by said photoacoustic system.

6. The system of claim 5, wherein said first laser energy of said first coagulation laser beam of said treatment laser is controlled by said photoacoustic system.

7. The system of claim 1, wherein said photoacoustic system further comprises a laser source configured to generate a light beam and direct said light beam towards said eye structure, said acoustic waves detected by said ultrasound transducer being generated as a result of the absorption of energy from said light beam of said laser source by said eye structure.

8. The system of claim 1, wherein said first laser-imaging system includes an eye tracking device configured to measure position and movement of an eye.

9. The system of claim 1, wherein said local control module includes a facial recognition device configured to verify an identity of a subject.

10. The system of claim 1, wherein said system includes a second laser-imaging system disposed at a third location, said second laser-imaging system being in communication with said central control system, and said second laser-imaging system including a second laser-imaging apparatus having a wide angle digital image acquisition system with at least one retinal viewing camera configured to acquire digital images of an eye structure.

11. The system of claim 1, wherein said wide angle digital image acquisition system comprises an elliptical mirror.

12. A system for laser coagulation of an eye structure, comprising:

a local control system disposed at a first location and a central control system disposed at a remote site, said remote site being at a second location, at least a first laser-imaging system disposed at said first location, said first laser-imaging system including a first laser-imaging apparatus, a laser generation system, a photoacoustic system, a first processor and a local control module, said first laser-imaging apparatus including a wide angle digital image acquisition system with at least one retinal viewing camera configured to acquire digital images of said eye structure, said local control module including local operation, local operation and performance simulation, and local safety and verification sub-modules;

a laser generation system including an aiming laser configured to generate and transmit an aiming laser beam to said eye structure, and a treatment laser configured to generate and transmit at least a first coagulation laser beam to said eye structure, said first coagulation laser beam having a first laser energy;

said local operation sub-module comprises a first computer configured and arranged to acquire at least a first eye structure image from said digital image acquisition system and transmit said first eye structure image to said remote site via a computer network, receive a target laser transmission area and laser transmission parameters from a remote physician via said computer network, apply an active contour algorithm to partition said first eye structure image into a grid map, execute a scatter laser coagulation of said eye structure using said treatment laser, acquire a plurality of post-procedure eye structure images, and transmit said post-procedure eye structure images to said remote site for evaluation and verification of treatment;

said photoacoustic system being operatively coupled to said laser generation system, said photoacoustic system including an ultrasound transducer configured to detect acoustic waves that are generated as a result of the absorption of energy by said eye structure such that said photoacoustic system is able to determine a temperature of said eye structure tissue subjected to said first laser energy, said ultrasound transducer comprising a transducer array configured to directionally target a reception of said acoustic waves, said photoacoustic system further being configured to control said laser generation system by maintaining said first laser energy of said first coagulation laser beam at a predetermined level so as to produce a uniform coagulation of said eye structure; and said central control system including a second processor and a remote control module, said remote control module including remote operation, remote operation and performance simulation, and remote safety and verification sub-modules, said remote operations sub-module comprising a computer configured and arranged to execute remote commands during a laser coagulation procedure on said eye structure in an actual control mode, wherein, in said actual control mode, said treatment laser is configured to transmit said first coagulation laser beam to said eye structure.

13. The system of claim 12, wherein said photoacoustic system comprises a laser source configured to generate a light beam and to direct said light beam towards said eye structure, said acoustic waves detected by said ultrasound transducer being generated as a result of the absorption of energy from said light beam of said laser source by said eye structure.

14. The system of claim 13, wherein said photoacoustic system further comprises an objective lens structure configured to be disposed between said laser source and said eye structure, said objective lens structure configured to adjust a focusing direction of said light beam of said laser source so as to enable the localization of a source of acoustic signals, said objective lens being operatively coupled to one or more micromechanical actuators, said one or more micromechanical actuators configured to displace said objective lens relative to said eye structure so as to target a particular line of points in said eye structure.

15. The system of claim 12, wherein said at least one retinal viewing camera of said digital image acquisition system provides a field of view of said eye structure between 150° and 200°.

16. The system of claim 12, wherein said wide angle digital image acquisition system comprises an elliptical mirror.

17. A system for laser coagulation of an eye structure, comprising:
a local control system disposed at a first location and a central control system disposed at a remote site, said remote site being at a second location,
at least a first laser-imaging system disposed at said first location, said first laser-imaging system including a first laser-imaging apparatus, a laser generation system, a photoacoustic system, a first processor and a local control module,
said first laser-imaging apparatus including a wide angle digital image acquisition system with at least one retinal viewing camera configured to acquire digital images of said eye structure, said local control module including local operation, local operation and performance simulation, and local safety and verification sub-modules;
a laser generation system including an aiming laser configured to generate and transmit an aiming laser beam to said eye structure, and a treatment laser configured to generate and transmit at least a first coagulation laser beam to said eye structure, said first coagulation laser beam having a first laser energy;
said local operation sub-module including a first computer configured and arranged to acquire at least a first eye structure image from said digital image acquisition system and transmit said first eye structure image to said remote site via a computer network, receive a target laser transmission area and laser transmission parameters from a remote physician via said computer network, apply an active contour algorithm to partition said first eye structure image into a grid map, execute a scatter laser coagulation of said eye structure using said treatment laser, acquire a plurality of post-procedure eye structure images, and transmit said post-procedure eye structure images to said remote site for evaluation and verification of treatment;

said photoacoustic system including a laser source configured to generate a light beam and to direct said light beam towards said eye structure and an ultrasound transducer configured to detect acoustic waves that are generated as a result of the absorption of energy from said light beam of said laser source by said eye structure such that said photoacoustic system is able to determine a temperature of said eye structure tissue subjected to said first laser energy, said ultrasound transducer comprising a transducer array configured to directionally target a reception of said acoustic waves, said photoacoustic system controlling said laser generation system by regulating said first laser energy of said first coagulation laser beam based upon said temperature of said eye structure tissue; and
said central control system including a second processor and a remote control module, said remote control module including remote operation, remote operation and performance simulation, and remote safety and verification sub-modules,
said remote operations sub-module comprising a second computer configured and arranged to execute remote commands during a laser coagulation procedure on said eye structure in an actual control mode, wherein, in said actual control mode, said treatment laser is configured to transmit said first coagulation laser beam to said eye structure.

18. The system of claim 17, wherein said photoacoustic system further comprises an objective lens structure configured to be disposed between said laser source and said eye structure, said objective lens structure configured to adjust a focusing direction of said light beam of said laser source so as to enable the localization of a source of acoustic signals, said objective lens being operatively coupled to one or more micromechanical actuators, said one or more micromechanical actuators configured to displace said objective lens relative to said eye structure so as to target a particular line of points in said eye structure.

19. The system of claim 17, wherein said at least one retinal viewing camera of said digital image acquisition system provides a field of view of said eye structure between 150° and 200°.

20. The system of claim 17, wherein said wide angle digital image acquisition system comprises an elliptical mirror.

* * * * *